United States Patent [19]

Bodor et al.

[11] 4,239,757

[45] Dec. 16, 1980

[54] THIAZOLIDINE PRODRUGS FOR THE IMPROVED DELIVERY OF ANTI-INFLAMMATORY CORTICOSTEROIDS

[75] Inventors: Nicholas S. Bodor, Gainesville, Fla.; Kenneth B. Sloan, Eudora, Kans.

[73] Assignee: INTERx Research Corporation, Lawrence, Kans.

[21] Appl. No.: 60,220

[22] Filed: Jul. 24, 1979

Related U.S. Application Data

[63] Continuation-in-part of Ser. No. 924,305, Jul. 13, 1978, abandoned.

[51] Int. Cl.³ .............................................. C07J 71/00
[52] U.S. Cl. .................................. 424/241; 260/239.5
[58] Field of Search ............................. 424/182, 241; 260/239.5

[56] References Cited

U.S. PATENT DOCUMENTS

| | | | |
|---|---|---|---|
| 3,542,770 | 11/1970 | Dekono | 260/239.5 |
| 3,562,255 | 2/1971 | Oliver et al. | 260/239.5 |
| 3,676,426 | 7/1972 | Clinton | 260/239.5 |

*Primary Examiner*—Elbert L. Roberts
*Attorney, Agent, or Firm*—Burns, Doane, Swecker & Mathis

[57] ABSTRACT

Novel 3,2'-spiro(1',3'-thiazolidine) compounds which are transient prodrug forms of known anti-inflammatory corticosteroids are disclosed. The subject compounds can be prepared by known methods, for example, by reacting the corresponding 3-keto steroids with a thiazolidine forming reagent such as an L-cysteine alkyl ester. Preferred compounds are derived from such known anti-inflammatory corticosteroids as cortisone acetate, hydrocortisone, prednisone, prednisolone and the like.

32 Claims, No Drawings

THIAZOLIDINE PRODRUGS FOR THE IMPROVED DELIVERY OF ANTI-INFLAMMATORY CORTICOSTEROIDS

CROSS-REFERENCE TO RELATED APPLICATION

This application is a continuation-in-part of our earlier copending application, Ser. No. 924,305, filed July 13, 1978, now abandoned, assigned to the assignee hereof and hereby expressly incorporated by reference in its entirety and relied upon.

TECHNICAL FIELD OF THE INVENTION

The present invention relates to certain selected novel 3,2'-spiro(1',3'-thiazolidine)steroids which are transient prodrug forms of conventional anti-inflammatory steroids (e.g., cortisone, hydrocortisone, prednisone, prednisolone, and the like) useful in alleviating inflammatory conditions in warm-blooded animals.

For purposes of this specification, the term "prodrug" denotes a derivative of a known and proven prior art anti-inflammatory steroid compound (e.g., cortisone, hydrocortisone, prednisone, prednisolone, or the like), which derivative, when administered to a warm-blooded animal, "cleaves" in such a manner as to release the proven drug form at its target site or sites of activity.

The term "transient" denotes enzymatic and/or chemical hydrolytic "cleavage" of the compounds of the instant invention in a manner such that the proven drug form (the conventional anti-inflammatory steroid, e.g., cortisone, hydrocortisone, prednisone, prednisolone, or the like) is released, while the remaining "cleaved" moiety remains nontoxic and is metabolized in such a manner that nontoxic, metabolic products are produced.

Finally, the term "pharmaceutically acceptable acid addition salt" as used herein generally includes the nontoxic acid addition salts of selected compounds of formula (I) or (II), formed with nontoxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, sulfonic, toluenesulfonic, and the like.

BACKGROUND OF THE PRIOR ART

Conventional anti-inflammatory steroids, such as cortisone, hydrocortisone, prednisone, prednisolone, and the like, are high molecular weight steroidal compounds containing a number of hydrophilic functions, e.g., hydroxyl and keto functions. These compounds are characterized as having (1) extremely low water solubility, (2) extensive intermolecular hydrogen bonding due to the combination of hydrophilic functions, such as —OH and =O (as evidenced by their high melting point), and (3) high molecular weight.

All three points enumerated above contribute to the inefficient and slow penetrability of these conventional steroidal compounds through biological barriers, among which the most important are (i) the skin and (ii) the gastrointestinal wall.

It is recognized that in the case of the skin, the high molecular weight anti-inflammatory steroids are absorbed primarily through the appendages and the hair follicles as opposed to the more efficient molecular intercellular absorption. See, M. Katz and B. J. Poulsen, "Absorption of Drugs through the skin," *Handbook of Experimental Pharmacology*, Vol. XXVII/I, Chapter 7, page 104, Springer Verlag, Berlin—Heidelberg—New York (1971).

It too is art recognized that (4) a serious side effect of certain of the known anti-inflammatory steroids is the decrease in thickness, or atrophy, of the skin at the site of application; that (5) another adverse effect is a deleterious, systemic side effect on the thymus gland; and that (6) in certain instances, with certain of the, e.g., hydrocortisone derivatives, the reduction of inflammation is inadequate.

In view of the foregoing, it is apparent that a serious need exists for a class of novel anti-inflammatory steroidal compounds which will overcome the aforementioned inefficiencies such that penetration of the same through biological barriers will be enhanced, such that less atrophy results, such that less effect on the thymus gland is evidenced, and such that inflammation is significantly reduced.

SUMMARY OF THE INVENTION

It is one object of the present invention to provide prodrug forms of conventional anti-inflammatory steroids which possess the capability of efficiently penetrating the biological barriers of warm-blooded animals, and, especially, the skin and the gastrointestinal wall.

Another object is the provision of prodrugs of conventional anti-inflammatory steroids which cause less atrophy, systemically effect the thymus to a much lesser degree, but which, nonetheless, remain highly potent.

It is another object of the present invention to provide such prodrug forms of conventional anti-inflammatory compounds which, following administration, will "cleave" in such a manner as to enable the original parent steroidal moiety (e.g., cortisone, hydrocortisone, prednisone, prednisolone, or the like) to be released at its therapeutic site or sites of anti-inflammatory activity and to further permit the cleaved moiety(ies) unassociated with the parent steroidal moiety to be metabolized in a nontoxic fashion.

All the foregoing objects are achieved by topically or orally administering to a warm-blooded animal afflicted with inflammation, a therapeutically effective anti-inflammatory amount of a compound having the structural formula:

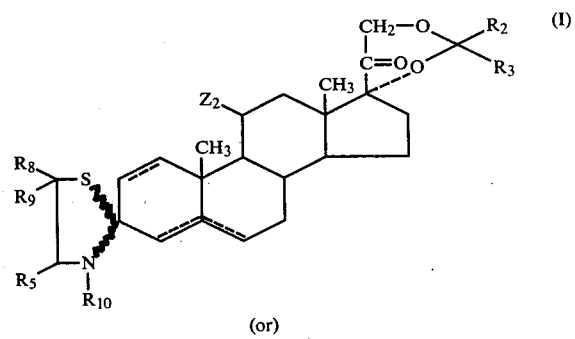

(or)

-continued

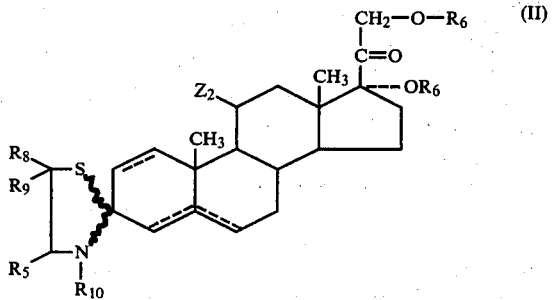

wherein $Z_1$ is =O or $\beta$-OH; $Z_2$ is =O, $\beta$—OH or $\beta$—OR$_1$; $R_1$ represents a radical of the formula:

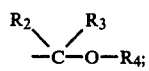

$R_4$ is H or $C_1$–$C_{10}$ alkyl; $R_2$ and $R_3$, which may be the same or different, are each H, $C_1$–$C_8$ alkyl, or substituted $C_1$–$C_8$ alkyl, wherein at least one of the hydrogen atoms therein has been replaced with a member selected from the group consisting of —N(R$_4$)$_2$, —CON(R$_4$)$_2$, a halogen atom (Cl, Br, I), —COOR$_4$, —COOCH$_2$N(R$_4$)$_2$ and —COOCH$_2$SR$_4$, wherein R$_4$ is defined as above, with the proviso that $R_2$ and $R_3$ cannot simultaneously be H; $R_2$ and $R_3$ can each further represent a radical of the formula:

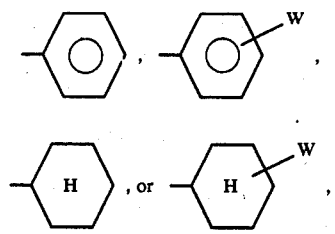

wherein W represents a member selected from the group consisting of —N(R$_4$)$_2$, —CON(R$_4$)$_2$, a halogen atom (Cl, Br, I), —COOR$_4$, —COOCH$_2$SR$_4$, wherein R$_4$ is defined as above; or $R_2$ and $R_3$ taken together can further represent —(CH$_2$)$_n$— wherein n is an integer of 5 to 7 and wherein one or more carbon atoms can optionally be replaced with a member selected from the group consisting of

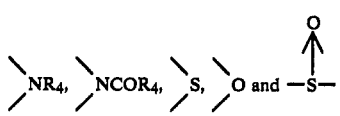

wherein R$_4$ is defined as above; R$_6$ is H or —COR$_7$, with the proviso that at least one of the R$_6$'s in formula (II) is H; R$_7$ is optionally substituted $C_1$–$C_{12}$ alkyl, optionally substituted $C_5$–$C_7$ cycloalkyl, optionally substituted $C_2$–$C_{12}$ alkenyl or optionally substituted $C_5$–$C_7$ cycloalkenyl; R$_7$ can further represent a radical of the formula:

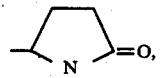

or an -alkylene-[CO]$_m$NR$_2$R$_3$ radical wherein m is 0 or 1, the alkylene portion is straight or branched and contains 1 to 6 carbon atoms and R$_2$ and R$_3$ are defined as before; or R$_7$ can be an imidazolyl or a 2-, 3- or 4- pyridyl group wherein at least one of the hydrogen atoms can optionally be replaced with a member selected from the group consisting of —N(R$_4$)$_2$, —CON(R$_4$)$_2$, —SOR$_4$, a halogen atom (Cl, Br, I), —COOR$_4$, —COOCH$_2$N(R$_4$)$_2$ and —COOCH$_2$SR$_4$ wherein R$_4$ is defined as above; or R$_7$ represents a radical of the formula:

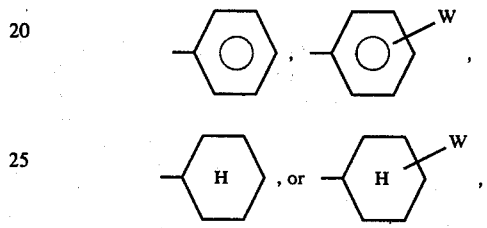

wherein W is defined as above; R$_8$ and R$_9$, which may be the same or different, are each H or $C_1$–$C_8$ alkyl; R$_5$ is —COOR$_{11}$; R$_{10}$ is H, —COR$_{11}$ or —COOR$_{11}$; R$_{11}$ is H, $C_1$–$C_{20}$ alkyl, $C_2$–$C_{20}$ alkenyl, $C_5$–$C_7$ cycloalkyl, $C_5$–$C_7$ cycloalkyl-aryl, phenyl or $C_1$–$C_4$ alkyl-substituted phenyl, with the proviso that when R$_{10}$ is H, then R$_{11}$ cannot be H or $C_1$–$C_4$ alkyl, and with the additional proviso that when R$_{10}$ is H, then the compound of formula (I) or (II) can be in the form of a pharmaceutically acceptable acid addition salt; the dotted line at the 1(2)-position indicates the optional presence of a double bond; and the dotted lines at the 4(5)-and 5(6)- positions indicate the presence of a double bond at either the 4(5)- or the 5(6) position.

With respect to formulas (I) and (II), it is to be noted that references to alkyl and alkenyl radicals encompasses straight and branched-chain groups containing the indicated number of carbon atoms.

DETAILED DESCRIPTION OF THE INVENTION

While all of the compounds encompassed by formulas (I) and (II) above essentially satisfy the objectives of the present invention, nevertheless, certain selected compounds as are set forth immediately below remain preferred:

(1) 21-Acetyloxy-11$\beta$,17$\alpha$-dihydroxypregn-4-en-20-one-3,2'-spiro(4'-carbohexoxy-1',3'-thiazolidine);

(2) 21-Acetyloxy-11$\beta$,17$\alpha$-dihydroxypregn-4-en-20-one-3,2'-spiro(4'-carbodecoxy-1',3'-thiazolidine);

(3) 21-Acetyloxy-11$\beta$,17$\alpha$-dihydroxypregn-5-en-20-one-3,2'-spiro(4'-carbohexoxy-1',3'-thiazolidine); and (4) 21-Acetyloxy-11$\beta$,17$\alpha$-dihydroxypregn-5-en-20-one-3,2'-spiro(4'-carbodecoxy-1',3'-thiazolidine).

It will be apparent to those skilled in the art that the preferred compounds listed above can be considered to be derived from hydrocortisone acetate. Other particularly suitable known anti-inflammatory corticosteroids from which the instant prodrugs can be derived include, but are not limited to, cortisone, hydrocortisone, prednisone, prednisone 21-acetate, prednisolone, prednisolone 21-acetate, cortisone acetate, prednisolone 21-tert-butylacetate, prednisolone 21-diethylaminoacetate, hydrocortisone tebutate and hydrocortamate. Thus, a particularly preferred group of compounds provided by the present invention can be represented by the formula:

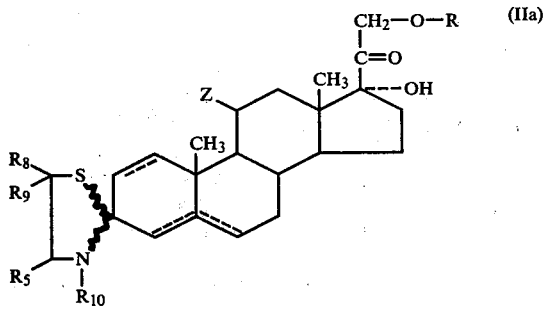

wherein $R_5$, $R_8$, $R_9$, $R_{10}$ and the dotted lines are as defined in claim 1, Z is =O or β—OH; and R is H, —CO—alkyl or —COCH$_2$N(alkyl)$_2$ wherein the alkyl groups each contain 1 to 8 carbon atoms. Most especially preferred are the compounds of formula (IIa) wherein $R_{10}$ is H and $R_5$ is —COOR$_{11}'$ wherein $R_{11}'$ is $C_5$-$C_{20}$ alkyl.

The compounds of the present invention are easily prepared, utilizing known techniques. (Compare generally our U.S. Pat. No. 4,069,322, assigned to the assignee hereof and expressly incorporated by reference herein.) Most conveniently, preparation involves contacting a compound corresponding to formula (I) or (II) but containing a 3-keto function, with a reagent of the formula:

wherein $R_5$, $R_8$ and $R_9$ are as hereinbefore defined, in the presence of a suitable organic solvent (e.g., benzene, toluene, xylene, dimethylformamide, or the like) and further in the presence of a suitable organic base (e.g., trimethylamine, triethylamine, pyridine, or the like). This reaction is carried out at standard pressure, at a temperature of from room temperature to the boiling point of the solvent employed and for a period of time ranging from approximately 2 to 48 hours. Alternatively, in this reaction, the organic base can serve as the solvent. In the course of the reaction, when the steroidal starting material is a $\Delta^4$ compound, the 4(5)-double bond sometimes migrates to the 5(6)-position. Generally, a mixture of $\Delta^4$ and $\Delta^{5(6)}$ compounds results. The nature of the particular reagent of formula (III), e.g., whether the reagent is used in the form of the free base or in the form of its hydrochloride salt, and the nature of the steroidal starting material can influence the location of the double bond, as can the manner of isolation of the final product. While control of reaction conditions and isolation techniques so as to afford the $\Delta^4$ compounds is preferred because the $\Delta^4$ compounds on hydrolysis go directly to the parent hormone, the $\Delta^{5(6)}$ derivatives are also highly desirable because they readily undergo hydrolysis and rearrangement of the double bond to the $\Delta^4$ parent hormone.

The compounds resulting from the process described above correspond to formulas (I) and (II) wherein $R_{10}$ is hydrogen. Further treatment of those products with a conventional acylating agent (e.g., acetic anhydride or propionic anhydride in pyridine) affords the corresponding compounds of the invention wherein $R_{10}$ is —COR$_{11}$ or —COOR$_{11}$.

A desirable alternate route to the compounds of formula (I) or (II) wherein the 1,2-linkage is unsaturated begins by reacting acetone with a reagent of formula (III) above. The product, a compound of the formula:

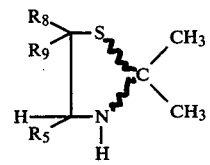

is then heated with a 3,20-diketosteroid, in the presence of an acid catalyst, using a large excess of the thiazolidine reactant, to effect transfer of the thiazolidine grouping to the steroid and provide the desired compound of formula (I) or (II).

The starting materials used in the preparation of the compounds of formulas (I) and (II) can be prepared by known methods; thus, for example, the methods set forth in Example 1 below are applicable to the preparation of various compounds of formula (III).

The invention will appear more fully from the examples which follow. These examples are given by way of illustration only and are not to be construed as limiting the invention either in spirit or in scope as many modifications both in materials and in methods will be apparent to those skilled in the art.

EXAMPLE 1

Illustrative Preparation of Starting Materials (a) L-Cysteine hexyl ester hydrochloride:

L-Cysteine hydrochloride (78.5 g) was added to 150 ml of hexanol saturated with dry HCl gas. The mixture was heated under reflux overnight. The solution was evaporated to about half of the total volume and then ethyl ether (150 ml) was added. The solution gave crystals when it was cooled. The crystals were filtered and were then recrystallized from ethyl acetate; yield 45 g; mp 89°–90° C.; IR (KBr) 1745 cm$^{-1}$; NMR (CDCl$_3$) δ 9.2–8.4 (b, 3, NH$_3$⊕), 4.7 (t, 1, —CH—), 4.3 (6, 2, —OCH$_2$—), 3.4 (b, 2, CH$_2$S—), 1.0–3.0 (m, 8), 1.0 (t, 3, CH$_3$).

Anal. Calcd for C$_9$H$_{20}$ClNO$_2$S: C, 44.69; H, 8.34; N, 5.79. Found: C, 44.80; H, 8.41; N, 5.69.

(b) L-Cysteine decyl ester hydrochloride:

L-Cysteine (157.4 g) was added to 250 ml of decyl alcohol saturated with dry HCl. The mixture was heated to 150° C. for 6 hours. The solution was cooled and then was mixed with an equal volume of ethyl acetate. The solution was cooled in a dry ice bath to give crystals. The crystals were filtered and were recrystallized from ethyl acetate, mp 96°–99° C., yield 100 g, IR (KBr) 1745 cm$^{-1}$; NMR (CDCl$_3$) δ 8.4–9.2 (b, 3, NH$_3$⊖), 4.7 (t, 1, —CH—), 4.3 (t, 2, —OCH$_2$—), 3.4 (b, 2, —CH$_2$S—), 1.0–3.0 (m, 16 —(CH$_2$)$_8$—), 2.6–2.8 (b, 1, SH), 1.0 (t, 3, CH$_3$—).

Anal. Calcd for C$_{13}$H$_{28}$NClSO$_2$: C, 52.51; H, 9.49; N, 4.71. Found: C, 52.20; H, 9.20; N, 4.80.

(c) Penicillamine ethyl ester hydrochloride and Penicillamine hexyl ester hydrochloride:

Dry hydrogen chloride was bubbled through a suspension of penicillamine (25 g, 0.167 mole) in 300 ml of dry ethanol until all was in solution. The warm solution was then cooled in an ice bath to 0°–5° C. and saturated with dry HCl. The ice bath was removed and the reaction mixture was heated to reflux for 2 hours, then was concentrated in vacuo to a viscous golden oil which was cooled (−30° C.) overnight. After warming to room temperature, the material, now a mixture of white crystalline solid and oil, was triturated with 500 ml Et$_2$O for 30 minutes, then was filtered. An insoluble oil passed through the filter funnel with the Et$_2$O and the residue was washed (3 times, 150 ml portions) further with Et$_2$O. After drying on the funnel under a stream of dry N$_2$, 14.14 g (mp 125°–145° C., 39% yield) of the desired product was obtained as white powder. NMR (CDCl$_3$) δ 8.85 (bs, 3, —NH$_3$Cl), 4.34 (q, 2, J=7 Hz, OCH$_2$—C), 4.6–4.15 (m, 1, NCHCO$_2$); 3.83 (s, 1, —SH), 1.70 (s, 3, C—CH$_3$), 1.59 (s, 3, C-CH$_3$), 1.35 (t, 3, J=7 Hz, OCH$_2$CH$_3$); IR (KBr) 1725 cm$^{-1}$ (s) (C=O).

Anal. Calcd for C$_7$H$_{16}$ClNO$_2$S: C, 39.34; H, 7.55; N, 6.56. Found: C, 39.04; H, 7.60; N, 6.47.

Similarly prepared from penicillamine and hexanol is penicillamine hexyl ester hydrochloride.

EXAMPLE 2

Preparation of 21-acetyloxy-11β,17α-dihydroxypregn-4-en-20-one-3,2'-spiro(4'-carboethoxy-5',5'-dimethyl-1',3'-thiazolidine) and 21-acetyloxy-11β,17α-dihydroxypregn-4-en-20-one-3,2'-spiro(4'-carbohexoxy-5',5'-dimethyl-1',3'-thiazolidine) and the corresponding Δ$^5$ compounds:

Hydrocortisone acetate (3.15 g) was dissolved in 80 ml of pyridine and allowed to react with penicillamine ethyl ester hydrochloride (10 g) under a nitrogen atmosphere at room temperature overnight. The pyridine was evaporated at <50° C. in vacuo (0.1 mm) and the residue was triturated with water for 4 hours. The suspension was filtered and the residue was dried. That crude product was dissolved in 20 ml of dichloromethane and the resultant solution was diluted to 100 ml with cyclohexane, then was concentrated on a hot plate to 30 ml. The solution was allowed to cool to room temperature under nitrogen, then the reaction vessel was stoppered tightly and left overnight. The precipitated material was filtered and washed once with a small amount of cyclohexane. After drying the material in vacuo (35°) for 2 hours, 2.22 g (mp 105°–107° C., 50% yield) of the desired product, a mixture of Δ$^4$ and Δ$^5$ compounds, was obtained: NMR (CDCl$_3$) δ 5.3 (s, 1, O=C—CH$_2$C—), 4.94 (ABq, 2, J$_{AB}$=17 Hz, Δ$_{ABv}$=12 Hz, O=C—CH$_2$—O), 4.24 (q, 2, J=7 Hz, —OCH$_2$CH$_3$), 2.14 (s, 3,) O—COCH$_3$), 1.61 (s, 3, C—CH$_3$), 0.89 (s, 3, C—CH$_3$); IR (KBr) 3600–3200 cm$^{-1}$ (b) (O—H), 3000–2800 cm$^{-1}$ (s) (C—H), 1715 cm$^{-1}$ (s) (C=O).

Anal. Calcd for C$_{30}$H$_{45}$NO$_7$S: C, 63.91; H, 8.05; N, 2.48.

Similarly prepared from hydrocortisone acetate and penicillamine hexyl ester hydrochloride is a mixture of 21-acetyloxy-11β,17α-dihydroxypregn-4-en-20-one-3,2'-spiro(4'-carbohexoxy-5',5'-dimethyl-1',3'-thiazolidine) and the corresponding Δ$^5$ compound.

EXAMPLE 3

Preparation of 21-acetyloxy-11β,17α-dihydroxypregn-4-en-20-one-3,2'-spiro(4'-carbohexoxy-1',3'-thiazolidine) and the corresponding Δ$^5$ compound This preparation was carried out in a manner identical to that of Example 2 using 5.2 g of hydrocortisone acetate and 17.5 g of L-cysteine hexyl ester hydrochloride, except that the recrystallized product was washed 3 times with 20 ml portions of hexane and dried under a stream of nitrogen to give 3.26 g of white powder which was the desired pure product (mp 149°–151° C., 42% yield), which was predominantly Δ$^4$ compound, but contained Δ$^5$ derivative also: NMR (CDCl$_3$) δ 5.23 (s, 1, O=C—CH=C), 4.95 (ABq, 2, J$_{AB}$—17 Hz, Δ$_{ABv}$=13 Hz, O=C—CH$_2$—O), 4.18 (bt, 2, O=C—OCH$_2$—), 2.15 (s, 3, —OCOCH$_3$), 1.33 (bs, 8, (CH$_2$)$_4$CH$_3$), 0.92 (s, 3, C—CH$_3$); IR (KBr) 3600–3300 cm$^{-1}$ (O—H), 2920 cm$^{-1}$, (s) (C—H), 1730 cm$^{-1}$1, 1710 cm$^{-1}$ (s) (C=O); [α]$^{24°}$ D= +78.2°, (C=0.5, EtOH.)

Anal. Calcd for C$_{32}$H$_{49}$SNO$_7$: C, 64.94; H, 8.35; N, 2.37. Found: C, 65.10; H, 8.50; N, 2.15.

EXAMPLE 4

Preparation of 21-acetyloxy-11β,17α-dihydroxypregn-4-en-20-one-3,2'-spiro(4'-carbodecoxy-1',3'-thiazolidine) and the corresponding Δ$^5$ compound To pyridine (50 ml) which was deoxygenated by boiling it and then allowing it to cool under nitrogen was added hydrocortisone (5 g, 13.8 mmoles). To the resulting solution was added L-cysteine decyl ester hydrochloride (22 g, 74 mmoles), which also dissolved. The resulting solution was stirred for 2 days under nitrogen. Pyridine was distilled from the reaction in vacuo to give a glassy, resinous residue, which was dissolved in 50 ml of dichloromethane. This solution was extracted three times with 140 ml portions of deoxygenated water and then was dried over sodium sulfate. The solution was filtered and the filtrate was concentrated in vacuo to a thick oil which solidified upon standing. The solidified oil was dissolved in 200 ml of hot ethanol and the solution was concentrated to 55 ml on a hot plate. The hot solution was removed from the heat and allowed to cool under nitrogen. After the flask had reached room temperature, it was tightly stoppered and placed in a freezer to crystallize overnight. The crystals which formed were filtered and washed once with a small amount of cold methanol, then were dried under a stream of nitrogen to give 2.07 g (26% yield, mp 142°–154° C.) of white powder which was the desired product (predominantly Δ$^4$ derivative but also containing Δ$^5$ compound): NMR (CDCl$_3$) δ 5.23 (s, 1, O=C—C(H)=C, 4.96 (ABq, 2, J$_{AB}$=24 Hz, Δ$_{ABz}$=15 Hz, O=C—CH$_2$—O), 4.20 (bt, 2, O=C—O—CH$_2$—), 2.16 (s, 3, —O—COCH$_3$), 1.30 (bs, 16, (CH$_2$)$_8$CH$_3$), 0.93 (s, 3, C—CH$_3$); IR (KBr) 3600–3300 cm$^{-1}$ (OH), 2920, 2840 cm$^{-1}$ (s) (C—H), 1732, 1710 cm$^{-1}$ (s) (C=O); [α]$^{25°}$ D= +73.5°, (C=0.5, EtOH.)

Anal. Caldd for C$_{26}$H$_{57}$NSO$_7$: C, 66.73; H, 8.87; N, 2.16. Found: C, 66.95; H, 9.25; N, 1.95.

EXAMPLES 5-39

Following the procedures indicated above, but substituting the appropriate specific reactants, affords the following additional compounds according to the invention:

COMPOUNDS OF FORMULA (I)

| Example Number | $Z_2$ | $R_2$ | $R_3$ | $R_5$ | $R_8$ | $R_9$ | $R_{10}$ | Δ |
|---|---|---|---|---|---|---|---|---|
| 5 | β—OH | —CH$_3$ | —CH$_3$ | —COOC$_6$H$_{13}$ | H | H | H | mixture of 4,5 and 5,6 |
| 6 | β—OH | —CH$_3$ | —CH$_2$CH$_2$—N(CH$_3$)$_2$ | —COOC$_6$H$_{13}$ | H | H | H | mixture of 4,5 and 5,6 |
| 7 | β—OH | H | —C$_6$H$_4$—N(CH$_3$)$_2$ | —COOC$_{10}$H$_{21}$ | H | H | H | mixture of 4,5 and 5,6 |
| 8 | β—OH | —CH$_2$CHN(CH$_3$)CH$_2$CH$_2$— | | —COOC$_{10}$H$_{21}$ | H | H | H | mixture of 4,5 and 5,6 |
| 9 | β—OH | —CH$_2$CH$_2$N(COCH$_3$)CH$_2$CH$_2$— | | —COOC$_6$H$_{13}$ | —CH$_3$ | —CH$_3$ | H | mixture of 4,5 and 5,6 |
| 10 | β—OH | —CH$_2$CH$_2$SO—CH$_2$CH$_2$— | | —COOC$_6$H$_{13}$ | —CH$_3$ | —CH$_3$ | H | mixture of 4,5 and 5,6 |
| 11 | =O | H | —C$_6$H$_4$—N(CH$_3$)$_2$ | —COOC$_6$H$_{13}$ | H | H | H | 1,2 & 4,5 |
| 12 | =O | —CH$_2$CH$_2$N(CH$_3$)CH$_2$CH$_2$— | | —COOC$_6$H$_{13}$ | H | H | H | 1,2 & 4,5 |
| 13 | =O | —CH$_2$CH$_2$N(COCH$_3$)CH$_2$CH$_2$— | | —COOC$_{10}$H$_{21}$ | H | H | H | 1,2 & 4,5 |
| 14 | =O | —CH$_2$CH$_2$SO—CH$_2$CH$_2$— | | —COOC$_{10}$H$_{21}$ | H | H | H | 1,2 & 4,5 |
| 15 | =O | —CH$_3$ | —CH$_3$ | —COOC$_6$H$_{13}$ | —CH$_3$ | —CH$_3$ | H | 1,2 & 4,5 |

COMPOUNDS OF FORMULA (II)

| Example Number | $Z_1$ | $R_6(17)$ | $R_6(21)$ | $R_5$ | $R_8$ | $R_9$ | $R_{10}$ | Δ |
|---|---|---|---|---|---|---|---|---|
| 16 | β—OH | H | H | —COOC$_6$H$_{13}$ | H | H | H | mixture of 4,5 and 5,6 |
| 17 | β—OH | H | —COCH$_2$N(CH$_3$)$_2$ | —COOC$_6$H$_{13}$ | —CH$_3$ | —CH$_3$ | H | mixture of 4,5 and 5,6 |
| 18 | =O | H | H | —COOC$_{10}$H$_{21}$ | H | H | H | mixture of 4,5 and 5,6 |
| 19 | =O | H | —COCH$_3$ | —COOC$_6$H$_{13}$ | H | H | H | 1,2 & 4,5 |
| 20 | =O | H | —COCH$_2$N(CH$_3$)$_2$ | —COOC$_6$H$_{13}$ | H | H | H | mixture of 4,5 and 5,6 |
| 21 | β—OH | H | H | —COOC$_{10}$H$_{21}$ | H | H | H | 1,2 & 4,5 |
| 22 | β—OH | H | —COCH$_3$ | —COOC$_{10}$H$_{21}$ | H | H | H | 1,2 & 4,5 |
| 23 | β—OH | H | —COCH$_2$N(CH$_3$)$_2$ | —COOC$_8$H$_{17}$ | H | H | H | 1,2 & 4,5 |
| 24 | =O | H | H | —COOC$_8$H$_{17}$ | H | H | H | 1,2 & 4,5 |
| 25 | =O | H | —COCH$_3$ | —COOC$_5$H$_{11}$ | H | H | H | mixture of 4,5 and 5,6 |
| 26 | β—OH | H | —COCH$_2$C(CH$_3$)$_3$ | —COOC$_5$H$_9$ | H | H | H | 1,2 & 4,5 |
| 27 | β—OH | H | —COCH$_2$N(C$_2$H$_5$)$_2$ | —COOC$_5$H$_9$ | —CH$_3$ | —CH$_3$ | H | 1,2 & 4,5 |
| 28 | β—OH | H | —COCH$_2$C(CH$_3$)$_3$ | —COOC$_5$H$_9$ | H | H | H | mixture of 4,5 and 5,6 |
| 29 | β—OH | H | —COCH$_2$N(C$_2$H$_5$)$_2$ | —COOC$_6$H$_{13}$ | H | H | H | mixture of 4,5 and 5,6 |
| 30 | β—OH | H | —CO—N(imidazolyl) | —COOC$_{10}$H$_{21}$ | H | H | H | mixture of 4,5 and 5,6 |
| 31 | β—OH | H | —COCH$_2$CH$_2$CON(CH$_3$)$_2$ | —COOC$_{10}$H$_{21}$ | H | H | H | mixture 4,5 and 5,6 |
| 32 | β—OH | H | —COCH$_2$CH$_2$CON(C$_2$H$_5$)$_2$ | —COOC$_6$H$_{13}$ | H | H | H | mixture of 4,5 and 5,6 |
| 33 | β—OH | H | —COCH$_3$CH$_2$CON(morpholino) | —COOC$_{10}$H$_{21}$ | H | H | H | mixture of 4,5 and 5,6 |
| 34 | β—OH | H | —CO-(N-H pyrrolidinonyl) | —COOC$_6$H$_{13}$ | —CH$_3$ | —CH$_3$ | H | mixture of 4,5 and 5,6 |
| 35 | =O | H | —CO—N(imidazolyl) | —COOC$_6$H$_{13}$ | —CH$_3$ | —CH$_3$ | H | 1,2 & 4,5 |
| 36 | =O | H | —COCH$_2$CH$_2$CON(CH$_3$)$_2$ | —COOC$_5$H$_9$ | H | H | H | 1,2, & 4,5 |
| 37 | =O | H | —COCH$_2$CH$_2$CON(C$_2$H$_5$)$_2$ | —COOC$_5$H$_9$ | H | H | H | 1,2 & 4,5 |
| 38 | =O | H | —COCH$_3$CH$_2$CON(morpholino) | —COOC$_5$H$_9$ | —CH$_3$ | —CH$_3$ | H | 1,2 & 4,5 |
| 39 | =O | H | —CO-(N-H pyrrolidinonyl) | —COOC$_6$H$_{13}$ | H | H | H | 1,2 & 4,5 |

The compounds of the present invention are conveniently administered to warm-blooded animals via conventional oral or topical administration with any suitable nontoxic pharmaceutically acceptable oral or topical inert carrier material. Such carrier materials are well-known to those skilled in the art of oral and topical pharmaceutical formulations. For those not skilled in the art, reference is made to the text entitled, "REMINGTON'S PHARMACEUTICAL SCIENCES", (Fourteenth Edition), 1970. In a typical preparation for oral administration, e.g., tablet or capsule, any one of the compounds of the instant invention is combined in an anti-inflammatory effective amount with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars, such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD&C dyes.

Similarly, in a typical formulation for topical application, any one of the compounds of the instant invention is combined with triacetin, such that the active ingredient is present in an anti-inflammatory effective amount. The preparation is simply applied topically to the inflamed area, whereby the therapeutically active compound is dermally absorbed and "cleaved" to release the parent steroidal moiety at the site of inflammation.

Naturally, the therapeutic dosage range for the compounds of the instant invention will vary with the size and needs of the patient. However, generally speaking, the following dosage guidelines will suffice. On an oral basis, the therapeutic dose required for a compound of the instant invention will generally, on a molecular basis, mimic that for the parent conventional steroid moiety (e.g., cortisone, hydrocortisone, prednisone, prednisolone, or the like). On a topical basis, application of an 0.01% to 2.5% concentration of a compound of the instant invention (in a suitable topical carrier material) to the site of inflammation should suffice.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What we claim is:

1. A compound having the structural formula

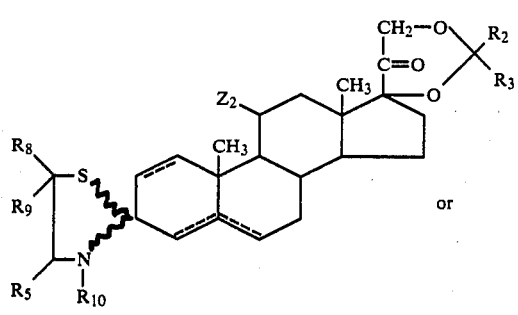

(I)

or

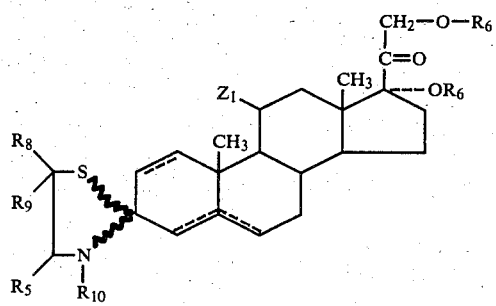

(II)

wherein $Z_1$ is $=O$ or $\beta$—OH; $Z_2$ is $=O$, $\beta$—OH or $\beta$—$OR_1$; $R_1$ represents a radical of the formula

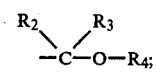

$R_4$ is H or $C_1$-$C_{10}$ alkyl; $R_2$ and $R_3$, which may be the same or different, are each $C_1$-$C_8$ alkyl, or substituted $C_1$-$C_8$ alkyl, wherein at least one of the hydrogen atoms therein has been replaced with a member selected from the group consisting of —$N(R_4)_2$, —$CON(R_4)_2$, a halogen atom (Cl, Br, I), —$COOR_4$, —$COOCH_2N(R_4)_2$ and —$COOCH_2SR_4$, wherein $R_4$ is defined as above; one of $R_2$ and $R_3$ can further represent H; $R_2$ and $R_3$ can each further represent a radical of the formula

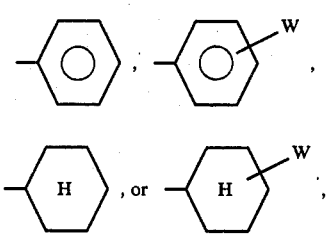

wherein W represents a member selected from the group consisting of —$N(R_4)_2$, —$CON(R_4)_2$, a halogen atom (Cl, Br, I), —$COOR_4$, —$COOCH_2N(R_4)_2$ and —$COOCH_2SR_4$, wherein $R_4$ is defined as above; or $R_2$ and $R_3$ taken together can further represent —$(CH_2)_n$— wherein n is an integer of 5 to 7, or —$(CH_2)_n$— wherein n is defined as above and wherein one or more carbon atoms has been replaced with a member selected from the group consisting of

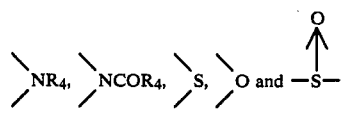

wherein $R_4$ is defined as above; $R_6$ is H or —$COR_7$, with the proviso that at least one of the $R_6$'s in formula (II) is H; $R_7$ is $C_1$-$C_{12}$ alkyl, $C_5$-$C_7$ cycloalkyl, $C_2$-$C_{12}$ alkenyl or $C_5$-$C_7$ cycloalkenyl, or substituted $C_1$-$C_{12}$ alkyl, substituted $C_5$-$C_7$ cycloalkyl, substituted $C_2$-$C_{12}$ alkenyl or substituted $C_5$-$C_7$ cycloalkenyl wherein the substituents are selected from the group consisting of —$N(R_4)_2$, —$CON(R_4)_2$, a halogen atom (Cl, Br, I), —$COOR_4$, —$COOCH_2N(R_4)_2$ and —$COOCH_2SR_4$, wherein R$_4$ is defined as above; R$_7$ can further represent a radical of the formula

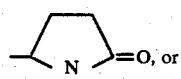

an alkylene-(CO)$_m$NR$_2$R$_3$ radical wherein m is 0 or 1, the alkylene portion is straight or branched and contains 1 to 6 carbon atoms and R$_2$ and R$_3$ are defined as before; or R$_7$ can be an imidazolyl or a 2-, 3- or 4-pyridyl group, or a substituted imidazolyl or 2-, 3- or 4-pyridyl group wherein at least one of the hydrogen atoms has been replaced with a member selected from the group consisting of —N(R$_4$)$_2$, —CON(R$_4$)$_2$, —SOR$_4$, a halogen atom (Cl, Br, I), —COOR$_4$, —COOCH$_2$N(R$_4$)$_2$ and —COOCH$_2$SR$_4$ wherein R$_4$ is defined as above; or R$_7$ represents a radical of the formula

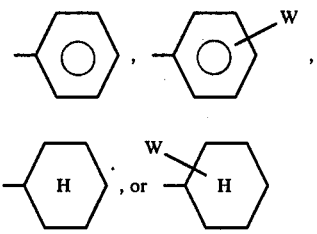

wherein W is defined as above; R$_8$ and R$_9$, which may be the same or different, are each H or C$_1$-C$_8$ alkyl; R$_5$ is —COOR$_{11}$; R$_{10}$ is H, —COR$_{11}$ or —COOR$_{11}$; R$_{11}$ is C$_5$-C$_{20}$ alkyl, C$_2$-C$_{20}$ alkenyl, C$_5$-C$_7$ cycloalkyl, C$_5$-C$_7$ cycloalkyl-aryl, phenyl or C$_1$-C$_4$ alkyl-substituted phenyl; when R$_{10}$ is other than H, then R$_{11}$ can also be H or C$_1$-C$_4$ alkyl; with the proviso that when R$_{10}$ is H, then the compound of formula (I) or (II) can be in the form of a pharmaceutically acceptable acid addition salt; the dotted line at the 1(2)-position indicates the presence of either a single or a double bond at the 1(2)-position; and the dotted lines at the 4(5)- and 5(6)-positions indicate the presence of a double bond at either the 4(5)- or the 5(6)-position.

2. A compound of claim 1, having the structural formula (I).

3. A compound of claim 2, wherein Z$_2$ is=O.

4. A compound of claim 2, wherein Z$_2$ is β—OH.

5. A compound of claim 2, wherein R$_2$ and R$_3$, which may be the same or different, are each selected from the group consisting of C$_1$-C$_8$ alkyl, substituted C$_1$-C$_8$ alkyl wherein the substituent is N(R$_4$)$_2$ wherein R$_4$ is H or C$_1$-C$_{10}$ alkyl, and

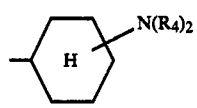

wherein R$_4$ is defined as above; or wherein one of R$_2$ and R$_3$ is H and the other of R$_2$ and R$_3$ is selected from the group consisting of C$_1$-C$_8$ alkyl, substituted C$_1$-C$_8$ alkyl wherein the substituent is N(R$_4$)$_2$ wherein R$_4$ is defined as above, and

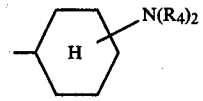

wherein R$_4$ is defined as above.

6. A compound of claim 2, wherein R$_2$ and R$_3$ are taken together to represent —(CH$_2$)$_n$— wherein n is an integer of 5 to 7, or —(CH$_2$)$_n$— wherein n is defined as above and wherein one of the carbon atoms has been replaced with a member selected from the group consisting of >NR$_4$ and >NCOR$_4$ wherein R$_4$ is H or C$_1$-C$_{10}$ alkyl.

7. A compound of claim 1, having the structural formula (II).

8. A compound of claim 7, wherein Z$_1$ is=O.

9. A compound of claim 7, wherein Z$_1$ is β—OH.

10. A compound of claim 7, wherein the R$_6$ portion of the 17α-substituent is H.

11. A compound of claim 7, wherein the R$_6$ portion of the 21-substituent is H.

12. A compound of claim 7, wherein both R$_6$'s are H.

13. A compound of claim 7, wherein the R$_6$ portion of the 21-substituent is —COR$_7$.

14. A compound of claim 13, wherein R$_7$ is C$_1$-C$_{12}$ alkyl.

15. A compound of claim 13, wherein R$_7$ is

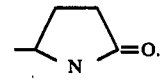

16. A compound of claim 13, wherein R$_7$ is an alkylene-[CO]$_m$NR$_2$R$_3$ radical.

17. A compound of claim 16, wherein R$_2$ and R$_3$, which may be the same or different, are each selected from the group consisting of H and C$_1$-C$_8$ alkyl.

18. A compound of claim 1, wherein double bonds are present in both the 1(2)- and the 4(5)-positions.

19. A compound of claim 1, wherein the steroid nucleus contains one double bond.

20. A compound of claim 19, wherein the double bond is present in the 4(5)-position.

21. A compound of claim 19, wherein the double bond is present in the 5(6)-position.

22. A compound of claim 1, wherein R$_5$ is —COOR$_{11}$ wherein R$_{11}$ is H or C$_1$-C$_{20}$ alkyl.

23. A compound of claim 1, wherein R$_8$ and R$_9$ are each H or CH$_3$.

24. A compound of claim 1, wherein R$_{10}$ is H and R$_{11}$ is C$_5$-C$_{20}$ alkyl.

25. A compound of claim 1 having the structural formula:

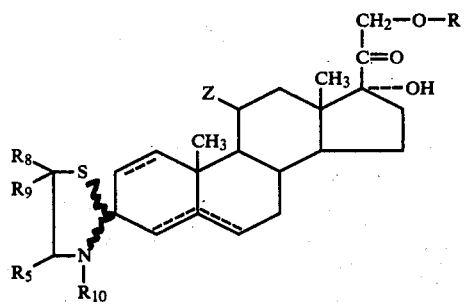 (IIa)

wherein $R_5$, $R_8$, $R_9$, $R_{10}$ and the dotted lines are as defined in claim 1, Z is =O or β—OH; and R is H, —CO-alkyl or —COCH$_2$N(alkyl)$_2$ wherein the alkyl groups each contain 1 to 8 carbon atoms.

26. A compound of claim 25 wherein $R_{10}$ is H and $R_5$ is —COOR'$_{11}$ wherein R'$_{11}$ is $C_5$–$C_{20}$ alkyl.

27. The compound of claim 1 which is 21-acetyloxy-11β,17α-dihydroxypregn-4-en-20-one-3,2'-spiro(4'-carbohexoxy-1',3'-thiazolidine).

28. The compound of claim 1 which is 21-acetyloxy-11β,17α-dihydroxypregn-5-en-20-one-3,2'-spiro(4'-carbohexoxy-1',3'-thiazolidine).

29. The compound of claim 1 which is 21-acetyloxy-11β,17α-dihydroxypregn-4-en-20-one-3,2'-spiro(4'-carbodecoxy-1',3'-thiazolidine).

30. The compound of claim 1 which is 21-acetyloxy-11β,17α-dihydroxypregn-5-en-20-one-3,2'-spiro(4'-carbodecoxy-1',3'-thiazolidine).

31. A pharmaceutical composition of matter comprising an anti-inflammatory effective amount of a compound of claim 1, in combination with a nontoxic, pharmaceutically acceptable, inert carrier therefor.

32. A method for alleviating inflammation in or on a warm-blooded animal exhibiting an inflammatory response, which comprises administering thereto an anti-inflammatory effective amount of a compound as defined by claim 1.

* * * * *